US010984236B2

(12) United States Patent
St-Hilaire et al.

(10) Patent No.: US 10,984,236 B2
(45) Date of Patent: Apr. 20, 2021

(54) SYSTEM AND APPARATUS FOR GAZE TRACKING

(71) Applicant: Mirametrix Inc., Montreal (CA)

(72) Inventors: Simon St-Hilaire, Montreal (CA); Nicholas Joseph Sullivan, Seattle, WA (US)

(73) Assignee: Mirametrix Inc., Montreal (CA)

( * ) Notice: Subject to any disclaimer, the term of this patent is extended or adjusted under 35 U.S.C. 154(b) by 0 days.

(21) Appl. No.: 16/015,608

(22) Filed: Jun. 22, 2018

(65) Prior Publication Data

US 2018/0300548 A1    Oct. 18, 2018

Related U.S. Application Data

(63) Continuation of application No. PCT/CA2016/051550, filed on Dec. 30, 2016.

(Continued)

(51) Int. Cl.
*G06K 9/00* (2006.01)
*G06F 3/01* (2006.01)
(Continued)

(52) U.S. Cl.
CPC .......... *G06K 9/00604* (2013.01); *A61B 3/113* (2013.01); *G06F 3/013* (2013.01); *G06K 9/2027* (2013.01)

(58) Field of Classification Search
None
See application file for complete search history.

(56) References Cited

U.S. PATENT DOCUMENTS 5,231,674 A    7/1993  Cleveland et al.
5,416,317 A *  5/1995  Nishimura ............. G03B 13/02
                                             250/221

(Continued)

FOREIGN PATENT DOCUMENTS

JP    06-230271 A    8/1994
JP    07-146432 A    6/1995
(Continued)

OTHER PUBLICATIONS

Khalid, L.; International Search Report from corresponding PCT Application No. PCT/CA2016/051550; dated May 8, 2017.
(Continued)

*Primary Examiner* — Kate H Luo
(74) *Attorney, Agent, or Firm* — Blake, Cassels & Graydon LLP; Laurie Wright; Christopher N. Hunter

(57) ABSTRACT

A system and an apparatus are provided, for gaze tracking within a defined operating range. The apparatus includes at least one optical system, which capable of capturing radiation in a wavelength range produced by a composite illumination source. The apparatus also includes at least one set of illumination sources creating the composite illumination source, wherein: at least one of the illumination sources is positioned relative to the optical system such that it ensures a user bright pupil response at the beginning of the apparatus operating range; and the composite illumination source size is such that it creates a Purkinje image on a user's eye capable of being distinguished by the optical system at the end of the apparatus operating range. The apparatus also includes an illumination controller for activating and deactivating the at least one composite illumination source, and a signal processing controller for transmitting generated images from the at least one optical system.

13 Claims, 7 Drawing Sheets

Related U.S. Application Data

(60) Provisional application No. 62/273,681, filed on Dec. 31, 2015.

(51) Int. Cl.
 *G06K 9/20* (2006.01)
 *A61B 3/113* (2006.01)

(56) References Cited

U.S. PATENT DOCUMENTS

| | | | |
|---|---|---|---|
| 5,790,234 A * | 8/1998 | Matsuyama | G03B 13/02 351/210 |
| 5,892,985 A * | 4/1999 | Matsuyama | G03B 13/02 348/78 |
| 7,572,008 B2 | 8/2009 | Elvesjo et al. | |
| 7,653,213 B2 | 1/2010 | Longhurst et al. | |
| 7,832,866 B2 | 11/2010 | Chao | |
| 8,135,173 B2 | 3/2012 | Chao | |
| 8,339,446 B2 | 12/2012 | Blixt et al. | |
| D722,315 S | 2/2015 | Liang et al. | |
| 9,185,196 B2 | 11/2015 | Guitteaud et al. | |
| 9,733,703 B2 | 8/2017 | Sullivan | |
| 2003/0223006 A1 | 12/2003 | Kito | |
| 2006/0110008 A1* | 5/2006 | Vertegaal | G06T 7/251 382/103 |
| 2013/0295994 A1* | 11/2013 | Guitteaud | F16M 13/04 455/556.1 |
| 2014/0071400 A1 | 3/2014 | Gao | |
| 2015/0085097 A1 | 3/2015 | Larsen | |
| 2015/0160726 A1* | 6/2015 | Sullivan | G02B 27/0093 345/156 |
| 2015/0301595 A1* | 10/2015 | Miki | A61B 3/113 715/847 |

FOREIGN PATENT DOCUMENTS

| | | |
|---|---|---|
| JP | 2004-7158 A | 1/2004 |
| JP | 2014-504762 A | 2/2014 |
| JP | 2014-86063 A | 5/2014 |
| JP | 2016-512626 A | 4/2016 |
| JP | 2016-512765 A | 5/2016 |
| WO | 2014/110469 A1 | 7/2014 |
| WO | 2014/0146199 A1 | 9/2014 |

OTHER PUBLICATIONS

Merchant, J. et al.; "Remote Measurement of Eye Direction Allowing Subject Motion Over One Cubic Foot of Space"; IEEE Transactions on Biomedical Engineering; BME-21(4); pp. 309-317; Jul. 1974.

Morimoto, C. et al.; "Pupil Detection and Tracking Using Multiple Light Sources"; Technical Report RJ 10117; IBM Almaden Research Center; 1998.

Ebisawa, Y.; Improved Video-Based Eye-Gaze Detection Method:; IEEE Transactions on Instrumentation and Measurement; 47(4); pp. 948-955; Aug. 1998.

Winn, B. et al.; "Factors Affecting Light-Adapted Pupil Size in Normal Human Subjects"; Invest Ophthalmol Vis Sci., 35(3); pp. 1132-1137; Mar. 1994.

Ji, Q. et al.; "Real-Time Eye, Gaze, and Face Pose Tracking for Monitoring Driver Vigilance"; Real-Time Imaging, 8(5); pp. 357-377; 2002.

Ohno, T. et al.; "FreeGaze: A Gaze Tracking System for Everyday Gaze Interaction"; In Proceedings of the 2002 Symposium on Eye Tracking Research & Applications, ETRA '02; pp. 125-132; 2002.

Sesma, L. et al.; "Evaluation of Pupil Center-Eye Corner Vector for Gaze Estimation Using a Web Cam"; In Proceedings of the symposium on eye tracking research and applications (ETRA 2010); pp. 217-220; 2012.

Grabner, H. et al.; "Tracking the Invisible: Learning Where the Object Might be"; In IEEE Conference on Computer Vision and Pattern Recognition, CVPR '10; pp. 1285-1292; Jun. 2010.

Japanese Publication 06-230271, English Counterpart U.S. Pat. No. 5,416,317.

Japanese Publication 2016-512765, English Counterpart U.S. Pat. No. 9,733,703.

Japanese Publication 2014-504762, English Counterpart U.S. Pat. No. 9,185,196.

Japanese Publication 2004-7158, English Counterpart US 2003/0223006.

Japanese Publication 2014-86063, English Counterpart US 2003/0301595.

Japanese Publication 2016-512626, English Counterpart WO 2014/110469.

English translation of Office Action dated Nov. 10, 2020 issued in connection with corresponding Japanese Application No. 2018-534876.

* cited by examiner

SYSTEM AND APPARATUS FOR GAZE TRACKING

CROSS-REFERENCE TO RELATED APPLICATION(S)

This application is a continuation of PCT Application No. PCT/CA2016/051550 filed on Dec. 30, 2016, which claims priority to U.S. Provisional Patent Application No. 62/273,681 filed on Dec. 31, 2015, both incorporated herein by reference.

TECHNICAL FIELD

The following relates to systems and apparatus for gaze tracking. More particularly to a minimal hardware complexity apparatus design and the gaze tracking systems incorporating same.

DESCRIPTION OF THE RELATED ART

The ability to remotely determine the gaze direction, albeit in a very constrained setting, was first reported in [1], in 1962. An apparatus for remote gaze tracking and pupillometry allowing the user to move freely within a 1 ft$^3$ head box was disclosed in [2], in 1974. The two aforementioned apparatuses are limited in use, as research tools, given the constraints imposed on the user and their reduced portability.

With the adoption of infrared illumination (referred to as active-IR in this context) of the subject's eyes, gaze tracking apparatuses take advantage of what is known as the bright-pupil response, the dark-pupil response, or both [3]. This coupled with adequate image processing can significantly improve both the robustness and the accuracy of the gaze estimation process.

The bright-pupil response under active-IR illumination is the infrared equivalent of the more widely known red-eye effect from photography, occurring when the light source used to illuminate the scene is positioned close to the camera's optical axis, so as to produce a retro-reflection from the retina. While in photography this is an undesired effect, in active-IR gaze tracking paradigms this is a means of improving the detectability of the pupil. The bright-pupil response is obtained by positioning the infrared illumination source(s) close to or coaxially (on-axis) with the camera lens. Conversely, the dark-pupil response is obtained by positioning the infrared illumination source(s) at a minimal distance away from the optical axis (off-axis) of the imaging device, avoiding the creation of a bright pupil response.

In common practice, a tandem of on-axis and off-axis infrared illuminators is used, as disclosed in [4] to ensure gaze tracking accuracy and robustness. This apparatus set-up is the current de facto solution for existing commercial gaze tracking solutions. Using both on-axis and off-axis illuminators requires a control circuitry for switching between the two, as well as a synchronization module to handle contiguous image acquisition.

On-axis-only approaches are less common, one such system and method, disclosed in [5], being limited to monocular gaze tracking and assuming the scene is constrained to the eye region. The use of this approach makes pupil detection straightforward since it relies on it to be the brightest object in the image given its expected size. However, the constrained field of view (FOV) and inherent variability in bright pupil responses highly limit the operating conditions under which such a system can be used.

One solution for taking advantage of the small form factor offered by an on-axis-only solution while mitigating the aforementioned limitations was first disclosed in [6]. In doing so, this exposed additional aspects of a gaze tracking apparatus that would benefit from this simplification. Particularly, minimizing the number of illumination sources and sensor resolution necessary to perform gaze tracking. Existing apparatuses still require a very large number of illumination sources to function, and high resolution sensors in order to image all the required components. It should be appreciated that, even when describing apparatuses that consist of one composite illumination source (e.g. a single off-axis source), existing apparatuses use a significant number of individual sources to create the defined composite source in an attempt to ensure the desired components on a user's eyes are detectable in the image.

SUMMARY

It is an object of the following to provide an apparatus capable of providing low resolution images that still contain sufficient detail to allow a gaze tracking system to use them. It is additionally an object of the present disclosure to define an apparatus with a minimal number of illumination sources necessary to ensure the desired eye components are detectable in said images.

In one aspect, there is provided an apparatus for gaze tracking within a defined operating range. The apparatus includes at least one optical system, which capable of capturing radiation in a wavelength range produced by a composite illumination source. The apparatus also includes at least one set of illumination sources creating the composite illumination source, wherein: at least one of the illumination sources is positioned relative to the optical system such that it ensures a user bright pupil response at the beginning of the apparatus operating range; and the composite illumination source size is such that it creates a Purkinje image on a user's eye capable of being distinguished by the optical system at the end of the apparatus operating range. The apparatus also includes an illumination controller for activating and deactivating the at least one composite illumination source, and a signal processing controller for transmitting generated images from the at least one optical system.

BRIEF DESCRIPTION OF THE DRAWINGS

Embodiments will now be described by way of example only with reference to the appended drawings wherein.

DETAILED DESCRIPTION

The feasibility of on-axis bright-pupil gaze tracking is dependent on having the provided on-axis bright-pupil system and the user environment meet a number of criteria:
   Minimum Viable Sensor Spatial Resolution,
   Illuminator Size/Positioning, and
   Image Quality.

Minimum Viable Sensor Spatial Resolution

A gaze tracking system relies on the ability to accurately extract particular image aspects of the eye, using these to estimate the user's point of gaze at any given instance of time. It is therefore essential that the sensor used meets minimal resolution constraints, such that it can distinguish said image aspects within a given scene throughout the full operating range.

Figure 1B:
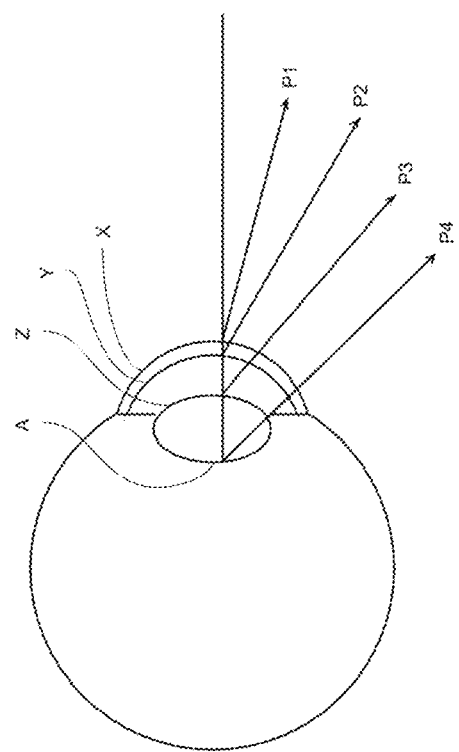
FIG. 1B illustrates the four Purkinje images as the reflections occurring when an incident light beam hits the human eye.
Figure 1A:
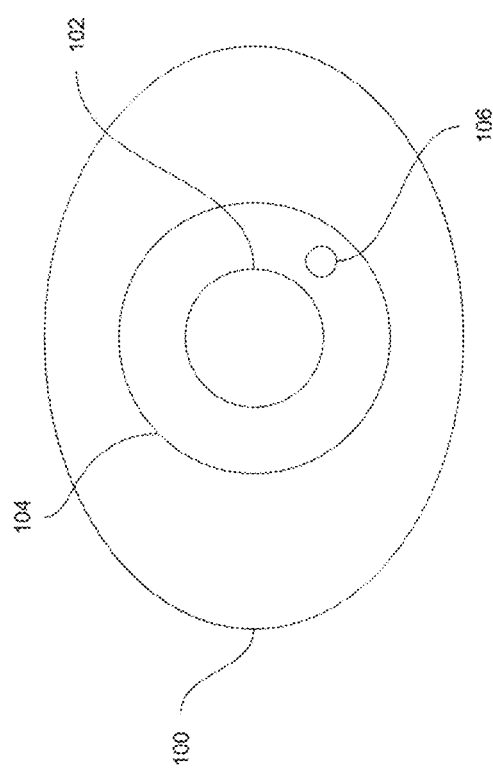
FIG. 1A illustrates the main human eye aspects used in active-IR gaze tracking.

FIG. 1A demonstrates an eye 100, and a number of key components of it. Particularly, the pupil 102 is visible within the iris, bounded by the limbus 104, which defines the border between the corneal surface and the sclera. Within this region, {104 ∪ 102}, an illumination source creates a specular reflection 106 on the cornea.

Although any number of image aspects may be used in conjunction with our described apparatus to track gaze, the apparatus design focuses on two key image aspects that guarantees image quality and resolution for the rest of the feature set: the pupil 102 and the corneal glint 106. By corneal glint we refer to the reflections of the system's illumination source on the anterior and posterior surfaces of the cornea, otherwise known as the 1st and 2nd Purkinje Images (or P1 and P2—see FIG. 1B). We focus on these image aspects, as they are assumed to correspond to the smallest image aspects of interest. Thus, a system that can distinguish the pupil and corneal glint should be able to resolve all other image aspects. This is achieved through image resolution and image quality constraints. For now, a focus on image resolution will be made.

It should be noted that an illumination source creates reflections on multiple surfaces of the human eye. The reflections of most interest are those denominated Purkinje images, illustrated in FIG. 1B. From Purkinje image 1 (P1) to image 4 (P4), these correspond respectively to reflections off of the: anterior surface of the cornea, posterior surface of the cornea, anterior surface of the crystalline lens, and posterior surface of the crystalline lens. Different combinations of the four Purkinje images are used by most active gaze tracking systems (i.e. where an illumination source is used; as opposed to a passive system, where it relies on external illumination to illuminate the scene), as they provide high accuracy and are more easily distinguishable in images than other image aspects. Intuitively, as light propagates through these multiple surfaces of the eye, its intensity decreases. Thus, the first two reflections, P1 and P2, are typically the most visible and extractable. We refer to these two in conjunction because they are usually indistinguishable by our defined apparatus. Due to the refraction properties of the anterior and posterior surfaces of the cornea, very minimal deviation occurs in the direction of a given ray. Additionally, because of the low resolution of the present system, the imaged reflection usually corresponds to a compound reflection, created from the merging of both P1 and P2.

With respect to the pupil, the apparatus should be able to detect a user's pupil throughout the defined operating range. For this, the variability in pupil diameter must be taken into account: according to [7], the pupil varies in diameter between 2-8 mm for the majority of the human population. This does not take into account the demagnification caused by viewing said pupil through the cornea. Because of this, it can be assumed the pupil will, at its smallest, be ~1 mm in diameter. The pupil can then be modeled as a 1D sinusoidal signal with a peak consisting of the pupil, and the trough consisting of background noise. The signal, then, would be 2 mm in wavelength.

At a minimum, the signal of interest must be differentiable within the spatial resolution range of the apparatus; that is, the signal must be distinguishable in pixel space. By the Nyquist-Shannon sampling theorem, we know that a signal is only characterizable if the sampling frequency is larger than twice the signal frequency. Thus, at the end of its operating range, the spatial resolution (SR) of our apparatus is at a minimum as follows:

$$SR_{min,pupil*} = \frac{\lambda_{pupil,px*}}{\lambda_{pupil,mm}} = \frac{2px}{2\ mm} = 1\frac{px}{mm} \quad (1)$$

The * symbol is appended to this calculation because, although theoretically accurate, the spatial resolution may still be too low. A general guideline for ensuring a signal is differentiable by an imaging system is to image it with at least 3 pixels, rather than 2. The pupil spatial resolution constraints can then be calculated as:

$$SR_{min,pupil} = \frac{\lambda_{pupil,px}}{\lambda_{pupil,mm}} = \frac{3px}{2\ mm} = 1.5\frac{px}{mm} \quad (2)$$

Returning to the corneal glint criterion, it should also be distinguishable throughout the operating range of the device. Of particular importance here is that the glint does not overly occlude the user's pupil. To account for this, an embodiment of the apparatus may restrict the illumination source size such that the glint is no more than 25% the size of the pupil signal for each dimension, so that accurate extraction of pupil image aspects is feasible under occlusion. Note that this would signify a 2D pupil signal with an area that is 16 times larger than the glint signal. Although this ratio could be considered quite large, it accounts for unknowns in the optics that may cause the specular reflection to appear larger.

To consider the sampling constraints, the corneal glint, 106, may be modeled as a 1D sinusoidal signal with a peak consisting of the glint maxima, and the trough consisting of the pupil intensity background. Assuming the illumination source approximates circular or square dimensions, and due to the near specular nature of reflections off of the cornea, this assumes a Gaussian signal for the corneal glint. Repeating the above-mentioned spatial resolution constraints, we can then define glint signal spatial resolution constraints as such:

$$SR_{min,glint*} = \frac{\lambda_{glint,px*}}{\lambda_{glint,mm}} = \frac{2px}{1\ mm} = 2\frac{px}{mm} \quad (3)$$

$$SR_{min,glint} = \frac{\lambda_{glint,px}}{\lambda_{glint,mm}} = \frac{3px}{1\ mm} = 3\frac{px}{mm} \quad (4)$$

Figure 5B:
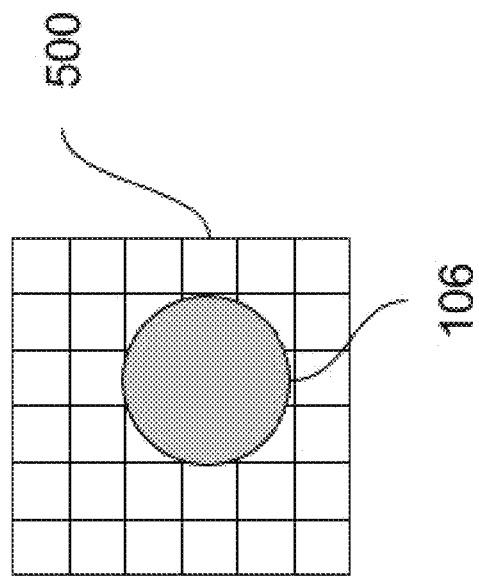
FIGS. 5A-5B illustrate the constraints on the illumination source size and the imaging sensor resolution, need in order to resolve the glint.
Figure 5A:
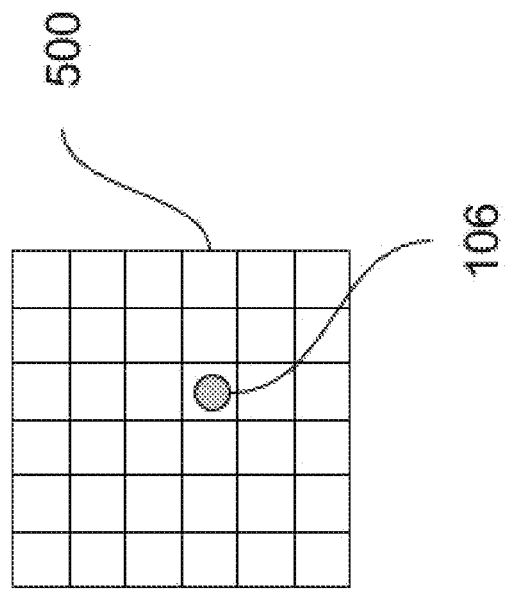

FIG. 5 illustrates these constraints on the illumination source size 208. FIG. 5A demonstrates a situation where an optical system with sensor resolution 500 is unable to properly detect the glint 106, as the glint is smaller than a single pixel of the sensor. FIG. 5B demonstrates a situation where an optical system with sensor resolution 500 is capable of detecting the glint 106, as the glint is significantly larger than the pixel size at said distance.

There is a key distinction between the glint and pupil constraints here: since the glint is a point source reflection, it contains a non-negligible added spread caused by the point spread function (PSF) of our apparatus' optical system. Additionally, as it is a reflection it will tend towards oversaturation, and will create a much larger contrast with the background than other objects in the scene. Because of these, an embodiment of the presently described apparatus should be able to consider the theoretical spatial resolution constraint and still be distinguishable in an image. This has been tested experimentally and found to be the case. That is, one can use the theoretical minimum, assuming a degree of PSF that will increase the signal. Put another way, the PSF can act as the "guideline" described above, to add an extra pixel for "safety".

It should be noted that the size of the corneal glint is directly proportional to the size of the illuminator (which will be discussed further below). However, due to the above mentioned occlusion issues, an embodiment of the apparatus may affix the minimum spatial resolution as a constant. Since it is clear that the limiting spatial resolution constraint on this embodiment of our apparatus is the glint signal, we can state the system spatial resolution constraint as:

$$SR_{min} = SR_{min,glint*} = 2\frac{px}{mm} \qquad (5)$$

It should be appreciated that the glint signal spatial resolution constraint can be loosened at the cost of higher glint-pupil occlusions. The scope of the described apparatus should not be limited by this fixed statement.

Illuminator Size/Positioning

The illuminator size is constrained by two criteria: the chosen sensor spatial resolution, and the positioning requirements for a bright pupil response. For a system to be gaze-tracking enabled in accordance with the presently described defined apparatus, it would need to pass both of these constraints.

FIG. 2 illustrates a number of embodiments of the described apparatus 200. All of these contain at least 2 components: an optical system 202 and a composite illumination source, consisting of individual illumination sources 204. The composite illumination source size is defined by 206, which ensures its corneal reflection can be imaged by the optical system throughout the operating range. Additionally, the distance between each illumination source and the optical system 208, ensures there is a bright pupil response throughout the operating range.

Figure 2C:
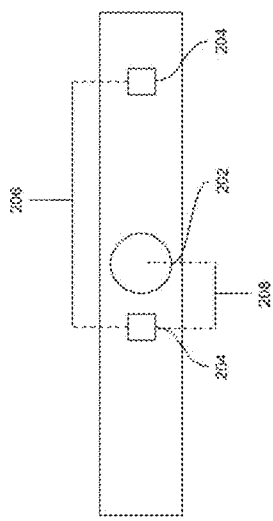
FIGS. 2A-2C illustrate embodiments of the disclosed apparatus.
Figure 2B:
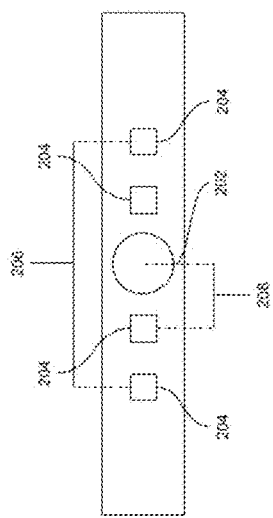
Figure 2A:
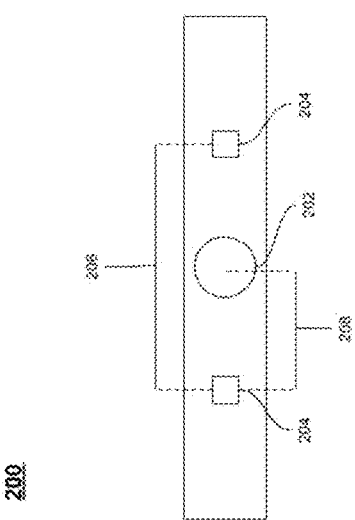

In FIG. 2A, a very simple embodiment of the apparatus is described. Here, the composite illumination source consists of two illumination sources 204, positioned symmetrically from the optical system 202, such that each of them is a distance 208 from it. This creates an effective illumination source of size 206, twice that of 208. The use of only 2 illumination sources placed symmetrically with respect to the sensor creates restrictions on the operating range of the device, as there will always be a trade-off between the region where a bright pupil response is expected, and the distance at which the glint can be detected. These will be explained further below.

Spatial Resolution Constraints

For a chosen minimal spatial resolution (spatial resolution at the end of the operating range), the illuminator size must be such that the corneal glint is visible and extractable. As discussed previously, the illuminator's size, would need to allow its corneal reflection to be larger than one pixel at the end of the operating range. Given the end range spatial resolution, $SR_{min}$ and the end of the operating range, $D_{z,max}$, the minimum illuminator size can be calculated by considering the specular reflection it would create off of the user's cornea. For this, the cornea may be modeled as a convex mirror, and the specular reflection considered as the size of the real image of the illuminator off said mirror. Thus, using convex mirror properties:

$$\frac{1}{f_{eye}} - \frac{1}{d_{object}} = \frac{1}{d_{image}} \qquad (6)$$

$$\frac{1}{f_{eye}} - \frac{1}{D_{z,max}} = \frac{1}{d_{image}}$$

$$d_{image} = \frac{D_{z,max} * f_{eye}}{D_{z,max} - f_{eye}}$$

Where $f_{eye}$ is the focal length of our eye model, $D_{z,max}$ is the maximum distance of the operating range (i.e. the object distance from the mirror), and $d_{image}$ is the determined distance of the real image. Note that the sign of our focal length is important; since one is dealing with a convex mirror, $f_{eye}$ should be negative.

Finally, the size of the corneal glint is obtained:

$$\frac{h_{image}}{h_{object}} = -\frac{d_{image}}{d_{object}} \qquad (7)$$

$$\frac{h_{image}}{h_{illuminator}} = -\frac{d_{image}}{D_{z,max}}$$

$$h_{illuminator,sr} = \frac{\frac{\lambda_{glint,mm}}{2} * D_{z,max}}{d_{image}}$$

With $h_{illuminator,sr}$ corresponding to the size of one side of the illuminator, in metric units, and $\lambda_{glint,mm}/2$ being the expected glint size at $D_{z,max}$. It is assumed that the illuminator is approximately square, and thus $h_{illuminator,sr}$ is a reasonable estimate of the size of the illuminator on both of its axes. It should be noted that, although the illuminator size can be increased, to increase the distance at which the corneal glint can be detected (and thus increase $D_{z,max}$) this will affect the occlusion effect the glint will have on the pupil.

"On-Axis" Positioning Constraints

In addition to the spatial resolution constraints described above, the illuminator positioning is restricted by the maximum illuminator-sensor distance under which a bright-pupil response is obtainable. This response occurs from illumination source light being transmitted through the human eye, reflecting off the choroid and retinal epithelium, and being transmitted back to the illumination source. A bright-pupil response is noticeable only when the illumination source is coaxial or nearly coaxial, causing a high percentage of the illumination source light to transmit directly into the optical system. As the illuminator is placed further away from the sensor, the bright pupil response of a user diminishes. This is principally due to the angular relationship between the illumination source, the eye, and the optical system, as shown in FIG. 4.

Figure 4:
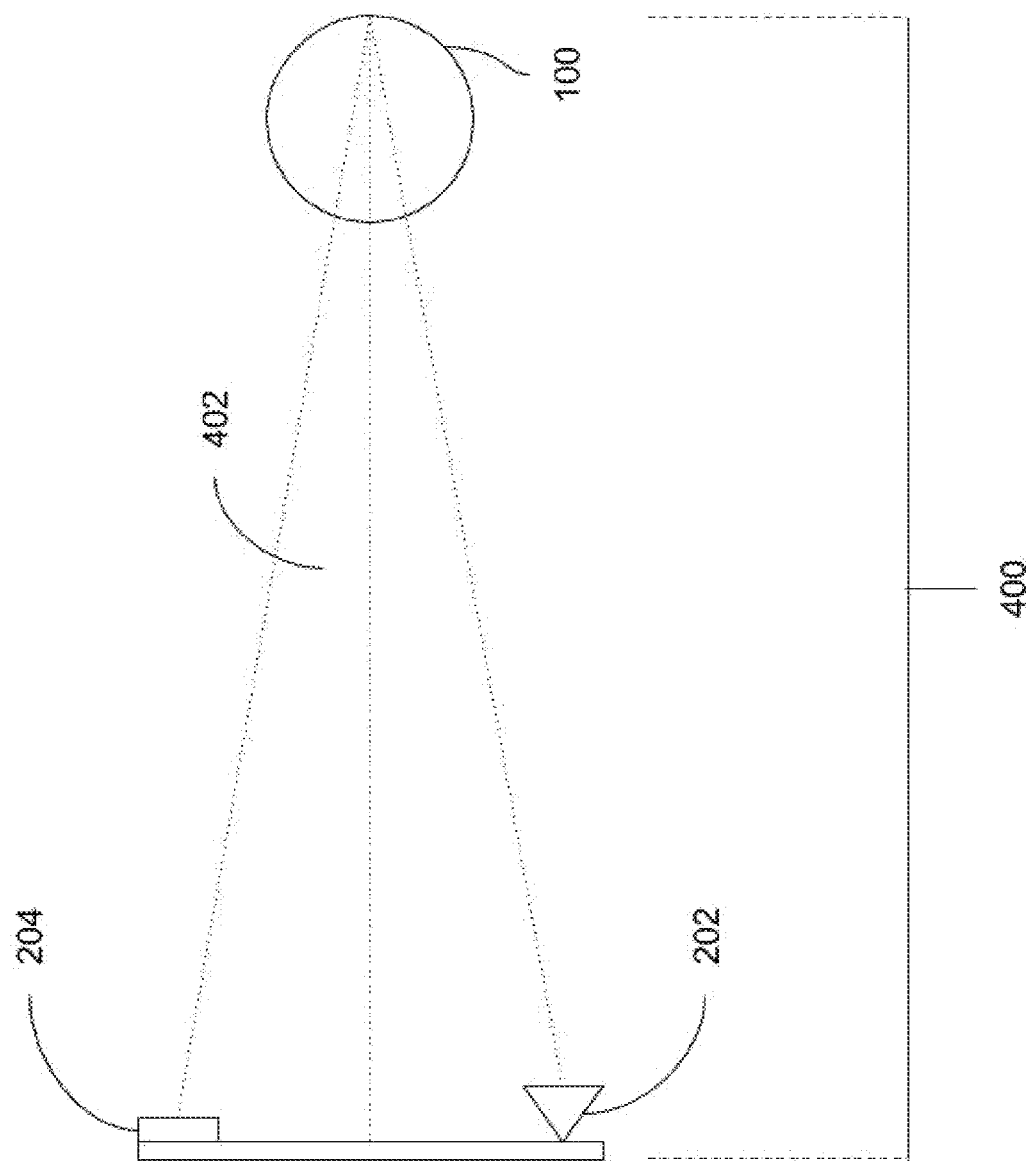
FIG. 4 illustrates the relationship between the apparatus and the user's eye so that it satisfies the bright-pupil requirements.

FIG. 4 visualizes the need for the composite illumination source being a distance 208 from the optical system. For a bright pupil response to occur, an illumination source 204 must approximate being coaxial to the optical system 202. For every distance 400 (in the defined operating range) that an eye 100 can be from the apparatus, the angle 402 created from the eye 100 to the illumination source 204 and optical system 202 must be minimal. Although no large-scale studies have been done on the necessary angular relationship to ensure a bright pupil response for the full human population, general guidelines exist and can be found within photography advice for avoiding the red-eye effect, a similar occurrence. For this, it is generally recommended to maintain an angular distance of at least 3 degrees at a given distance, to avoid obtaining red eye. From extensive testing, this recommendation seems to be too large, likely due to the fact that photographers merely wish to remove red eye effect, rather than attempt to maximize the effect. Through testing, it has been determined that the angle 402 should be less than 0.5 degrees throughout the operating range, to ensure a bright pupil response on all users within the operating range. Thus, given the beginning of the desired operating range, $D_{z,min}$, the maximum distance an illumination source can be from the sensor for a bright pupil response, $h_{illuminator,bp}$, can be defined as:

$$h_{illuminator,bp} = 2*\tan(\theta_{bp})*D_{z,min}$$

$$\theta_{bp} = 0.5 \text{ deg} \quad (8)$$

Note that this heuristic does not guarantee a bright pupil response, but is used to attempt to maximize the users for which a bright pupil response will be apparent throughout the operating range. The multiple parameters that can affect this (e.g. pupil constriction rate, external illumination) may still remove the bright-pupil response for a particular user and scenario.

Image Quality

As stated previously, for an embodiment of the apparatus, the minimum required feature to be extracted from the optical system is a 0.5 mm diameter 2D point source reflection. This situation presents two problem scenarios which need to be taken into account:

The actual background the signal is consistently over is sufficiently high that the signal is lost in the background.

The input signal is spread over enough pixels on the sensor that it is indistinguishable from its background.

The image quality requirements brought by these will be explained further below.

BACKGROUND CRITERIA

Normally, the MTF (Modulation Transfer Function) ratio is calculated assuming a standard sinusoidal signal peaking at the top of the range. However, the feature of importance is often surrounded by a larger signal, that of the pupil reflection. Thus, to ensure our estimate takes this into account, one can calculate the effective ratio needed around a glint's peak, to permit the desired contrast ratio. A sample embodiment will consider a contrast ratio of 3:2.

Assuming the peak of a one dimensional cutoff of the signal is at index 1, and the major spread caused by our optical system occurs at indexes 0 and 2, we focus on the relationship between indices 1 and 2. It is our desire that the contrast between $I_1$ and $I_2$ be 3:2. Additionally, we can expect that the intensity $I_1$ will consist of the pupil intensity, $I_P$, and the glint intensity, $I_G$. Finally, the intensity $I_2$ will consist of the pupil intensity, $I_P$, and the point-spread effect of the glint intensity $I_G$ on index 2, $PSF(D_1)I_G$ (the desired PSF ratio multiplied by the signal). Thus, we have the following equations:

$$\frac{I_1}{I_2} = \frac{3}{2} \quad (9)$$

$$I_1 = I_P + I_G$$

$$I_2 = I_P + PSF(D_1)I_G$$

Thus:

$$I_2 = I_P + PSF(D_1)I_G \quad (10)$$

$$\frac{2}{3}I_1 = I_P + PSF(D_1)I_G$$

$$\frac{2}{3}I_1 = I_1 - I_G + PSF(D_1)I_G$$

$$PSF(D_1)I_G = I_G - \frac{1}{3}I_1$$

$$PSF(D_1) = \frac{I_G - \frac{1}{3}I_1}{I_G}$$

Since this is dealing with a point source, one can make the assumption that $I_G$. Thus, for the sample embodiment described, one can calculate the PSF effect on index 2 to be 0.66. That is, the point spread function of our system should be, at most, spread to its adjacent pixel at an intensity ratio of 1:0.66.

Signal Spread Criteria

In order to ensure our signal is not lost, one should be certain that a sinusoidal signal equivalent to it in amplitude can be extracted from the optical system. Thus, a sine wave of amplitude spanning the full range, and wavelength equivalent to twice the signal size must be distinguishable by our system. Here, we will use the embodiment spatial resolution constraint described earlier, namely $$SR_{min} = 2\frac{px}{mm}.$$

The frequency cutoff of our system, then, is 1 lp/mm (line pair per millimeter). Thus:

$$\frac{1\frac{lp}{mm}}{2\frac{px}{mm}} = 0.5\frac{\text{cycles}}{px} \quad (11)$$

Using this value and a sample sensor's pixel size, 1.4 μm², the final requirement value is computed. It is important to note that since the previous requirements are stated as diagonals, the diagonal size of the pixel ($\sqrt{1.4\mu m^2 + 1.4\mu m^2} = 1.98$ μm) will be used.

$$\text{Cutoff} = \frac{0.5 \frac{\text{cycles}}{\text{pix}}}{1.98 \ \mu m} = \frac{0.5 \frac{\text{cycles}}{\text{pix}}}{1.98 \times 10^{-3} \ \text{mm}} \qquad (12)$$

$$\text{Cutoff} = 252.54 \frac{lp}{\text{mm}}$$

As elaborated previously, the neighboring pixels of the 1 pixel signal should be no more than 0.66 (ratio of 3:2) of the peak value of the signal. The Modulation Transfer Function (MTF) is thus calculated:

$$MTF = \frac{I_{max} - I_{min}}{I_{max} + I_{min}} = \frac{1 - 0.66}{1 - 0.66} = 0.20 \qquad (13)$$

Apparatus Designs

Returning to FIG. 2A, it is evident that restricting our composite illumination source to two sources enforces a trade-off between the minimum and maximum distances at which the apparatus will obtain usable images. The former is caused by the distance 208 that each illumination source is from the optical system, which ensures the bright pupil response. The latter is determined by the composite illumination source size 206 (assuming a fixed resolution), which defines where the minimal spatial resolution will be met.

In fact, given a fixed sensor resolution, it is not possible to symmetrically position the two sources and guarantee that a desired operating range can be met. The main limitation that the design of FIG. 2A creates is one of flexibility: the module must be designed with the illumination source distance 208 defined by $h_{illuminator,\ bp}$ in order to guarantee the operating range. However, doing so implies a significantly larger required sensor resolution or significantly smaller lens field-of-view (FOV) than what would be necessary with the other configurations.

To clarify further, we will describe a sample procedure for designing the described apparatus:

1. Define the desired operating range, [$D_{z,min}$, $D_{z,max}$], and the minimal required spatial resolution, $SR_{min}$, for the system to function.
2. According to the apparatus design, define the positioning of the illumination sources to meet the operating range.
3. Define a sensor and lens combination that ensures the minimum spatial resolution constraint, $SR_{min}$, is met or surpassed.

It should be clear that the designs described herein principally considers step 2. The design of FIG. 2A creates an added step between 2 and 3: we must update the spatial resolution constraints to account for the defined illumination source positioning. This is because the glint size at the end of the operating range, $\lambda_{glint,mm}$, will likely be much smaller as it is created from a smaller composite source. Thus, $SR_{min}$ must be redefined according to the smaller expected glint signal.

It is worth noting that step 3 in the sample procedure may be constrained further. As an example, there may be a desired minimum head box throughout the operating range. In such a situation, the sensor resolution will need to be increased significantly to meet or exceed $SR_{min}$.

In FIG. 2B, the composite illumination source consists of four illumination sources 204, again positioned symmetrically from the optical system 202. In this embodiment, however, there are two symmetrically positioned sources close to the optical system, and two further away. These define inner and outer source pairs, respectively. The inner source pairs ensure a strong bright pupil response throughout the operating range via their distance 208, while the outer source pairs ensure the glint can be detected throughout the same range. With this embodiment, both considerations are maximized. The exact positioning can be found for the inner source pairs $h_{illuminator,bp}$ for the outer source pairs, via $h_{illuminator,sr}$. Unfortunately, this doubles the number of illumination sources required for a particular apparatus, which may be unrealistic due to manufacturing costs.

In FIG. 2C, the four illumination sources are simulated by two illumination sources 204, positioned asymmetrically from the optical system. Thus, one of these is positioned at a distance 208 from the optical system 202, to create the bright pupil response throughout the operating range. The other one is positioned such that the composite illumination source is of size 206. The exact positioning can be found in a similar manner as that of FIG. 2B, with the inner source set via $h_{illuminator,bp}$, and the distance between the two sources set via $h_{illuminator,sr}$. This minimizes the number of illumination sources required to guarantee a bright pupil response and detectable glint throughout the operating range of the apparatus.

Figure 3C:
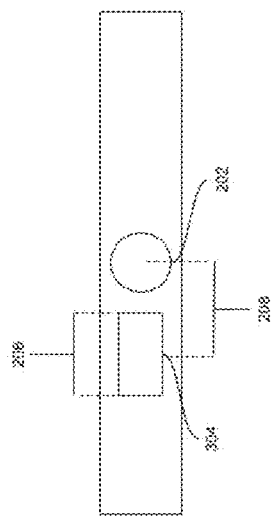
FIGS. 3A-3C illustrate additional embodiments of the disclosed apparatus.
Figure 3B:
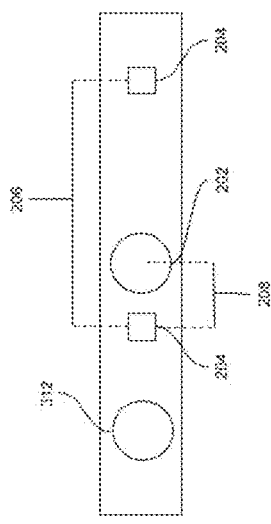
Figure 3A:
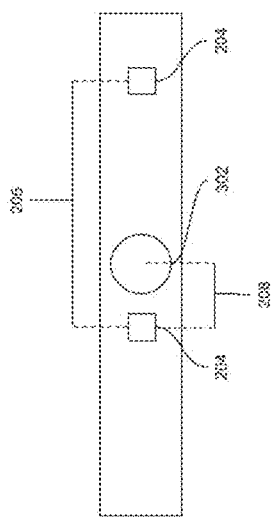

FIG. 3 describes some alternative apparatus implementations. In FIG. 3A, the optical system 202 is replaced with an optical system 302, capable of detecting additional wavelengths, for purposes outside of gaze tracking. Thus, for example, as opposed to only detecting the wavelength range associated with the illumination source, the system also detects visual spectrum data. This allows the gaze tracking apparatus to function both as a gaze tracking system, and as a standard webcam. In FIG. 3B, the system described in FIG. 2C is expanded with an optical system 312, capable of detecting visual spectrum information. Thus, it serves the same purpose of the apparatus in FIG. 3A, with separate optical systems. In FIG. 3C, the composite illumination source is defined by a single, large illumination source 304. Thus, the single illumination source is of size 206, and positioned at a distance 208 from the optical system 202. The illumination source 304 can, for example, consist of a high-power, large size LED, or a laser projector.

Figure 6:
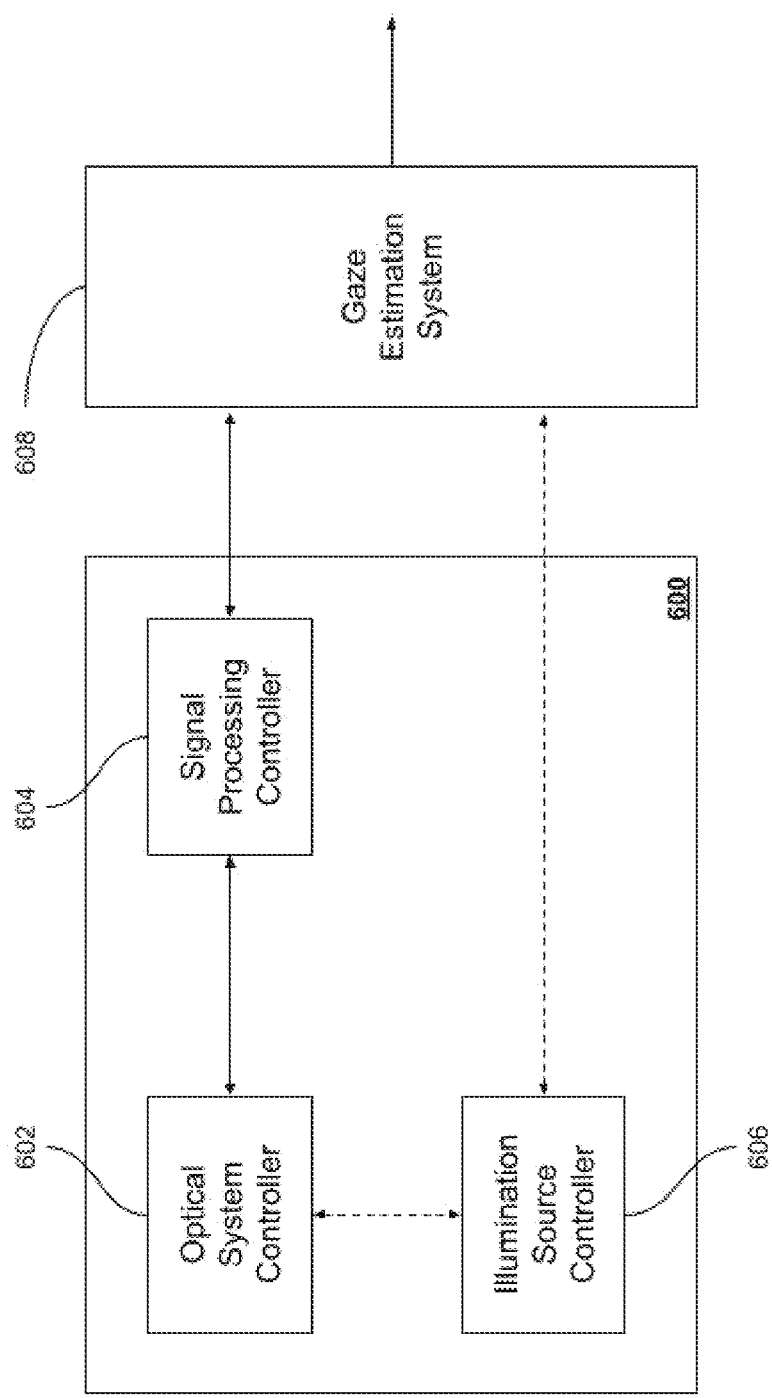
FIG. 6 illustrates an embodiment of the disclosed system and apparatus therein.

FIG. 6 shows the apparatus logic 600. Here, an optical system controller, 602, requests an image acquisition and receives the sensor results once the acquisition has completed. It additionally controls optical system parameters, such as shutter speed, analog signal gain, and frame rate. A signal processing controller, 604, receives the images and performs any requisite processing on the image before it is sent out to a gaze estimation system 608. An illumination source controller, 606, ensures the illumination sources are powered on when required for image acquisition. An embodiment of it can control the effective illumination source output power, so as to ensure the correct amount of light is sent to the user. This component is optionally connected to the optical system controller and/or gaze estimation system. If the former, it can ensure synchronization between image acquisition and illumination sources, to minimize power consumption. Additionally, it can simulate effective illumination on the user via the optical system parameters. This allows the system to maintain the illumination source as low as possible while ensuring a useful image. If the latter, the illumination source controller can receive illumination change requests from the gaze estimation system itself. This would allow the image to always be corrected to what the gaze estimation system defines as an "ideal" image.

An alternative embodiment of the apparatus additionally uses the illumination source controller, 606, in conjunction with the optical system controller, 602, for ambient illumination subtraction via image differencing. In this case, the apparatus captures images with the illumination source sequentially alternating on and off. In doing so, the "on" image contains ambient illumination, as well as illumination from the described illumination source; the "of" image only contains ambient illumination in the scene. For each pair of images, the "on" image is then difference with the "off" image to create an image which that minimizes the ambient illumination from it. This addition may be used to minimize the effect ambient illumination has on the captured images, allowing the apparatus to function in more extreme ambient illumination. It should be apparent that such an embodiment requires control logic to synchronize the alternating illumination Source with the image acquisition. It shall be appreciated that the differencing logic can be performed by the signal processing controller, 604, the gaze estimation system, 608, or by a separate entity in between the described apparatus and the gaze estimation system.

Figure 7:
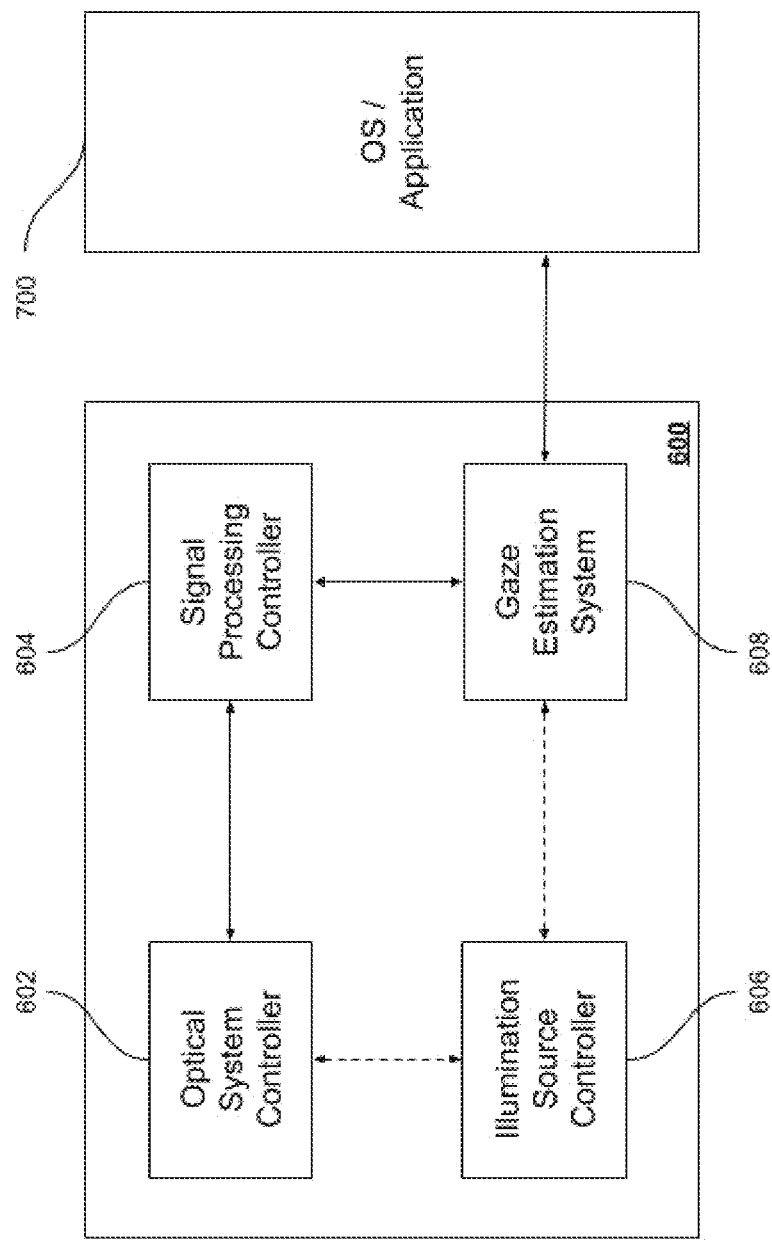
FIG. 7 illustrates another embodiment of the disclosed system and apparatus therein.

In FIG. 7, we see another embodiment of the apparatus logic. In this case, the gaze estimation system, 608, is within the apparatus logic 600. The device outputs gaze information directly to an operating system or application 700, with all the computation being done within the apparatus.

REFERENCES

[1] A. L. Yarbus. Eye Movements and Vision. *New York: Plenum,* 1967 (originally published in Russian 1962).

[2] J. Merchant, R. Morrissette, and J. L. Porterfield. Remote measurement of eye direction allowing subject motion over one cubic foot of space. *IEEE Transactions on Biomedical Engineering*, BME-21(4):309-317, July 1974.

[3] C. Morimoto, M. Flickner, A. Amir, and D. Koons. Pupil detection and tracking using multiple light sources. Technical Report RJ 10117, IBM US Research Centers (Yorktown, San Jose, Almaden, US), Yorktown Heights, 1998.

[4] Y. Ebisawa. Improved video-based eye-gaze detection method. *IEEE Transactions on Instrumentation and Measurement,* 47(4):948-955, August 1998.

[5] D. Cleveland, J. H. Cleveland, P. L. Norloff. Eye tracking method and apparatus. July 1993. U.S. Pat. No. 5,231, 674.

[6] N. J. Sullivan. System and method for on-axis eye gaze tracking. September 2014. WO Patent App. PCT/CA2014/050,282.

[7] B. Winn, D. Whitaker, D. B. Elliott, N. J. Phillips. Factors affecting light-adapted pupil size in normal human subjects. *Invest Ophthalmol Vis Sci.,* 35(3):1132-1137, March 1994.

For simplicity and clarity of illustration, where considered appropriate, reference numerals may be repeated among the figures to indicate corresponding or analogous elements. In addition, numerous specific details are set forth in order to provide a thorough understanding of the examples described herein. However, it will be understood by those of ordinary skill in the art that the examples described herein may be practiced without these specific details. In other instances, well-known methods, procedures and components have not been described in detail so as not to obscure the examples described herein. Also, the description is not to be considered as limiting the scope of the examples described herein.

It will be appreciated that the examples and corresponding diagrams used herein are for illustrative purposes only. Different configurations and terminology can be used without departing from the principles expressed herein. For instance, components and modules can be added, deleted, modified, or arranged with differing connections without departing from these principles.

It will also be appreciated that any module or component exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the systems and/or devices described herein, any component of or related thereto, or accessible or connectable thereto. Any application or module herein described may be implemented using computer readable/executable instructions that may be stored or otherwise held by such computer readable media.

The steps or operations in the flow charts and diagrams described herein are just for example. There may be many variations to these steps or operations without departing from the principles discussed above. For instance, the steps may be performed in a differing order, or steps may be added, deleted, or modified.

Although the above principles have been described with reference to certain specific examples, various modifications thereof will be apparent to those skilled in the art as outlined in the appended claims.

The invention claimed is:

1. An apparatus for gaze tracking by measuring a bright pupil response and a Purkinje image within a defined operating range, a beginning of the operating range being a minimum distance between an optical system and a user, an end of the operating range being a maximum distance between the optical system and the user, the apparatus comprising:
   a. the optical system, the optical system being capable of capturing radiation in a wavelength range produced by a composite illumination source;
   b. at least two illumination sources creating the composite illumination source, wherein:
      i. at least one of the illumination sources is positioned sufficiently close to the optical system for the user to exhibit a bright pupil response at the beginning of the operating range; and
      ii. at least another one of the illumination sources is positioned such that: the composite illumination source is large enough to create a Purkinje image on an eye of the user that is distinguishable by the optical system at the end of the apparatus operating range, at a chosen required spatial resolution; and the composite illumination source is small enough for the optical system to distinguish the Purkinje image from the bright pupil response throughout the operating range;
   c. circuitry for conveying electrical signals to the composite illumination source; and d. circuitry for transmitting generated images from the optical system.

2. The apparatus of claim 1, wherein the composite illumination source comprises any of the following: light-emitting diodes (LED), lasers, and laser projectors.

3. The apparatus of claim 1, wherein the at least one optical system contains an RGB-IR sensor.

4. The apparatus of claim 1, wherein the at least one optical system contains a monochrome sensor.

5. The apparatus of claim 4, wherein the monochrome sensor only accepts radiation in the wavelength range of the composite illumination source.

6. The apparatus of claim 1, wherein the composite illumination source comprises two illumination sources, placed asymmetrically from the optical system, wherein the size and positioning constraints are maintained.

7. The apparatus of claim 1, wherein the composite illumination source comprises four illumination sources, wherein:
 a. two of the illumination sources are positioned symmetrically from the optical axis, such that they create a user bright pupil response at the beginning of the apparatus operating range; and
 b. two of the illumination sources are positioned symmetrically from the optical axis, with the distance between them to create a Purkinje image on a user's eye capable of being distinguished by the optical system at the end of the apparatus operating range.

8. The apparatus of claim 1, further comprising a processing unit for performing gaze estimation methods.

9. Image data provided by an apparatus of claim 1, wherein said data comprises at least one of a user's eyes,
 c. wherein said eye comprises:
  i. a bright pupil response, or
  ii. a corneal glint, or
  iii. a bright pupil response and a corneal glint
 d. wherein said data is used for:
  i. gaze tracking purposes, be it online, offline, onsite, or offsite; or
  ii. any other application that makes use of the bright pupil response, the glint, or both, be it directly or indirectly.

10. The apparatus of claim 1, further comprising a non-transitory computer readable medium containing instructions for activating and deactivating the composite illumination source via the circuitry.

11. The apparatus of claim 10, wherein the instructions define the emitted power of the composite illumination source.

12. The apparatus of claim 1, further comprising a non-transitory computer readable medium containing instructions for transmitting generated images from the optical system via the circuitry.

13. The apparatus of claim 12, wherein the instructions define image quality parameters to be modified, and control said image parameters.

* * * * *